United States Patent
Cook et al.

[11] Patent Number: 5,213,111
[45] Date of Patent: May 25, 1993

[54] COMPOSITE WIRE GUIDE CONSTRUCTION

[75] Inventors: William A. Cook; Scott E. Eells, both of Bloomington, Ind.

[73] Assignee: Cook Incorporated, Bloomington, Ind.

[21] Appl. No.: 728,233

[22] Filed: Jul. 10, 1991

[51] Int. Cl.⁵ .................... A61B 5/00; A61M 25/00
[52] U.S. Cl. ........................... 128/772; 604/281
[58] Field of Search ............... 604/170, 281, 282, 95; 128/657, 772

[56] References Cited

U.S. PATENT DOCUMENTS

| | | | |
|---|---|---|---|
| 3,749,086 | 7/1973 | Kline et al. | 128/2 |
| 4,380,574 | 4/1983 | Gessinger et al. | 428/686 |
| 4,654,092 | 3/1987 | Melton | 148/402 |
| 4,748,986 | 6/1988 | Morrison et al. | 128/772 |
| 4,846,186 | 7/1989 | Box et al. | 128/657 |
| 4,867,173 | 9/1989 | Leoni | 128/772 |
| 4,884,579 | 12/1989 | Engelson | 128/772 |
| 4,925,445 | 5/1990 | Sakamoto et al. | 60/95 |
| 4,964,409 | 10/1990 | Tremulis | 128/657 |
| 4,971,490 | 11/1990 | Hawkins | 128/772 |
| 4,984,581 | 1/1991 | Stice | 128/772 |
| 5,025,799 | 6/1991 | Wilson | 128/772 |
| 5,052,407 | 10/1991 | Hauser et al. | 128/786 |
| 5,069,217 | 12/1991 | Fleishhacker, Jr. | 128/657 |
| 5,069,226 | 12/1991 | Yamauchi et al. | 128/772 |
| 5,095,915 | 3/1992 | Engelson | 128/772 |
| 5,109,830 | 5/1992 | Cho | 128/4 |
| 5,111,829 | 5/1992 | Alvarez de Toledo | 128/772 |
| 5,129,890 | 7/1992 | Bates et al. | 604/281 |

*Primary Examiner*—John D. Yasko
*Assistant Examiner*—Adam J. Cermak
*Attorney, Agent, or Firm*—Woodard, Emhart, Naughton, Moriarty & McNett

[57] ABSTRACT

A wire guide construction for medical procedures that involve accessing specific inner body areas without major surgery. The wire guide comprises a mandrel which is a coaxial composite of a thin stainless steel wire radially surrounded by a shape memory alloy, such as a nickel titanium alloy. The mandrel is of a constant diameter over the majority of its length except it is tapered at its distal end to reveal the inner stainless steel wire. A flexible coil of platinum is attached near the distal end of the mandrel and is secured in place when a smoothly rounded tip is welded to the distal tip of the mandrel. The complete wire guide can be coated with a polymer layer, and 70 to 80% of the distal portion of the wire guide can be coated with a hydrophilic polymer to increase lubricity.

29 Claims, 3 Drawing Sheets

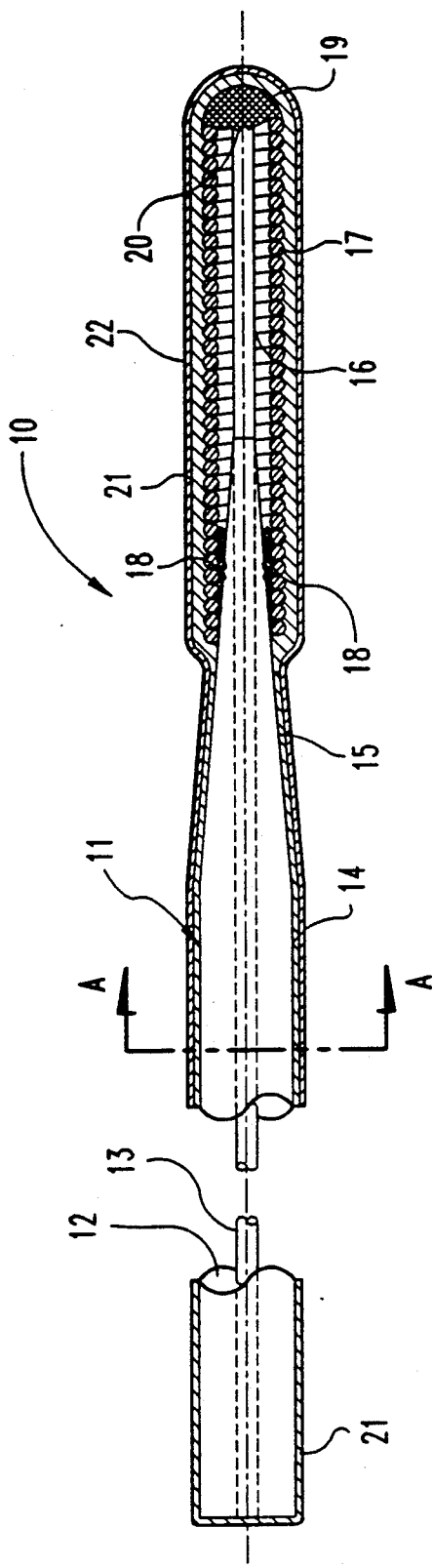
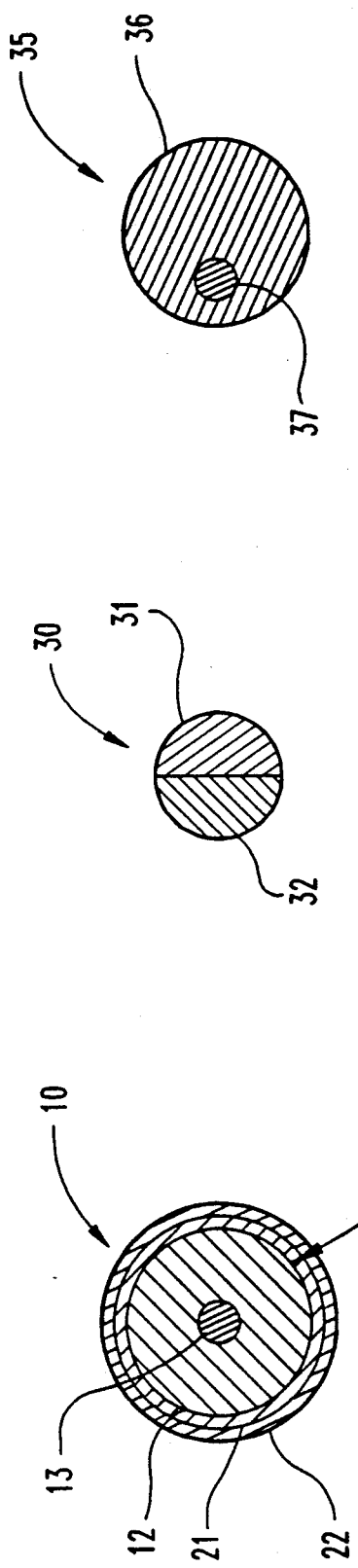
Fig. 1
Fig. 3
Fig. 4
Fig. 2

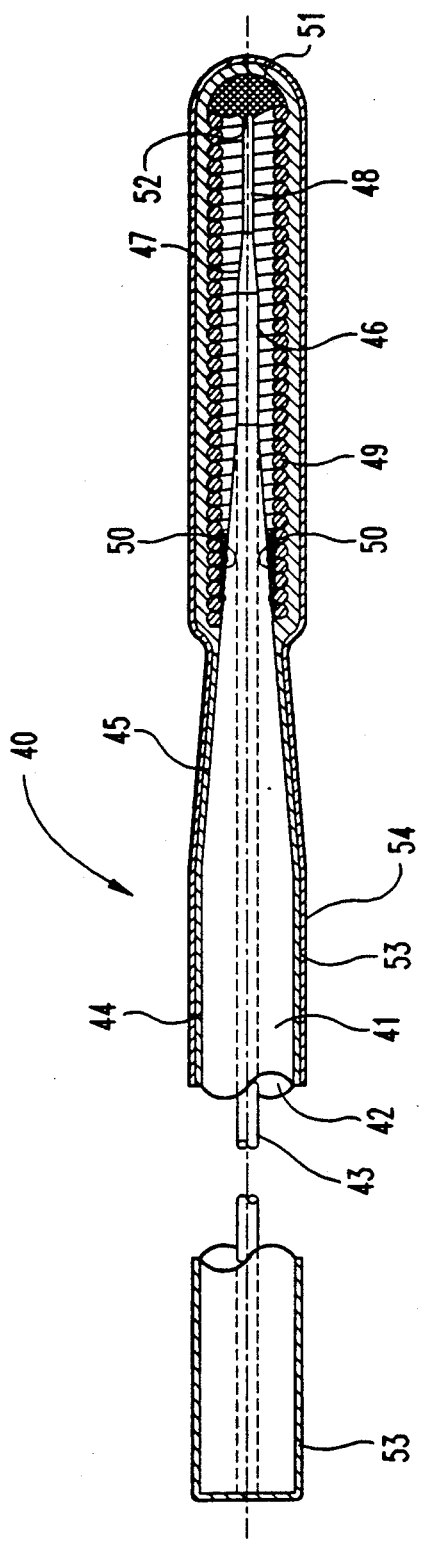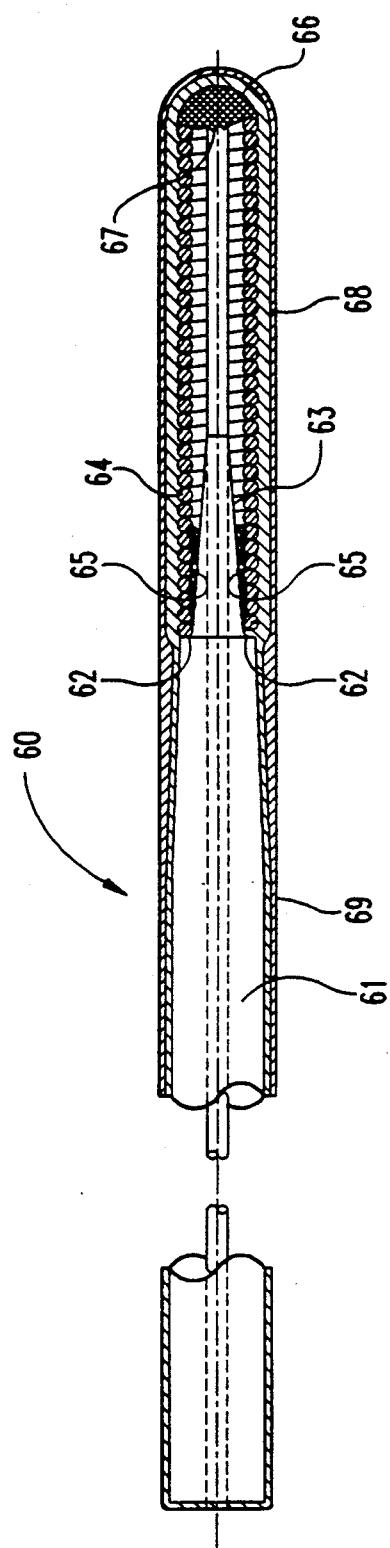

COMPOSITE WIRE GUIDE CONSTRUCTION

BACKGROUND OF THE INVENTION

This invention relates generally to wire guides used to position a catheter or other medical tool at a precise location within a patient.

Wire guides are used routinely in various medical procedures. In order to negotiate a tortuous path or avoid obstacles during insertion, wire guides normally include a floppy tip that is often biased in a certain direction. However, it is desirable that the remaining portion of the wire guide be somewhat elastic and resistant to kinking but still able to transmit a torque so that the doctor can change the direction of the biased tip to make a turn or avoid an obstacle while advancing the wire guide into position. It has been found that using a shape memory material, such as a nickel titanium (NiTi) alloy, in the body of the wire guide has significant advantages over conventional steel wire guides in that NiTi's "super elastic" properties can allow doctors to reach much more remote locations within the body. In other words, certain nickel titanium alloys are simply more kink resistant than conventional stainless steel. Unfortunately, however, NiTi alloys are not easily bonded to other materials, making it troublesome to use in manufacturing the distal tip of the wire guide.

In order to obtain a desired flexibility at the tip, wire guides are often tapered at their distal end, and often include a coil spring extending over the tapered portion and a smoothly rounded tip attached at the distal end of the mandrel. The smoothly rounded tip must normally be welded to the mandrel. However, because NiTi alloys are generally not easily bonded to other metals, attaching the rounded tip to a NiTi mandrel is a difficult procedure.

What is needed is a mandrel for wire guides which is substantially kink resistant over the majority of its length but which also retains the manufacturing advantages and reliability of stainless steel at its distal end.

SUMMARY OF THE INVENTION

One embodiment of the present invention might include a composite mandrel for a wire guide having a strand of weldable material radially surrounded by and fused with a shape memory material. The strand is preferably coaxial with the shape memory material but could also be off center or eccentric. Also, the strand is preferably formed from stainless steel but could also be formed of some radiopaque material, such as gold or platinum. The shape memory material is preferably a nickel titanium alloy. The shape memory material improves kink resistance over the body of the mandrel, while the strand of weldable material is exposed at the distal tip of the mandrel to facilitate bonding other components, such as a smoothly rounded cap, to the distal end of the mandrel.

In another embodiment of the present invention there is provided a wire guide having a composite mandrel of memory shape material and a readily weldable material. The mandrel is machined at its distal end so that only the readily weldable material is exposed. The wire guide includes a flexible coil coaxially surrounding a portion of the distal end of the mandrel, and a smoothly rounded tip is welded to the distal end of the mandrel distally of the flexible coil. Finally, the entire length of the wire guide is coated with a first polymer coating, and the distal 70 to 80% of the wire guide includes a second hydrophilic coating which adds lubricity.

In still another embodiment of the present invention there is provided a wire guide having a composite mandrel of memory shape material and a readily weldable material. The distal end of the mandrel is tapered to increase flexibility. The entire length of the wire guide is then coated with a polymer, wherein the coating is made thicker at the distal end to provide the desired flexibility. The distal 70 to 80% of the wire guide is then coated with a hydrophilic coating to increase lubricity.

One object of the present invention is to provide an improved wire guide.

Another object of the present invention is to provide a wire guide having the advantages of a shape memory material but which retains the advantages of conventional steel wire guides.

Related objects and advantages of the present invention will be apparent from the following description.

BRIEF DESCRIPTION OF THE DRAWINGS

FIG. 1 is a fragmentary longitudinal sectional view of a wire guide according to the preferred embodiment of the present invention.

FIG. 2 is a cross section of the wire guide of FIG. 1 along section A—A of FIG. 1 in the direction of the arrows.

FIG. 3 is a cross section of a mandrel for a wire guide according to another embodiment of the present invention FIG. 4 is a cross section of a mandrel for a wire guide according to still another embodiment of the present invention.

FIG. 5 is a fragmentary longitudinal sectional view of a wire guide according to another embodiment of the present invention.

FIG. 6 is a fragmentary longitudinal sectional view of a wire guide according to another embodiment of the present invention.

DESCRIPTION OF THE PREFERRED EMBODIMENT

Figure 7:
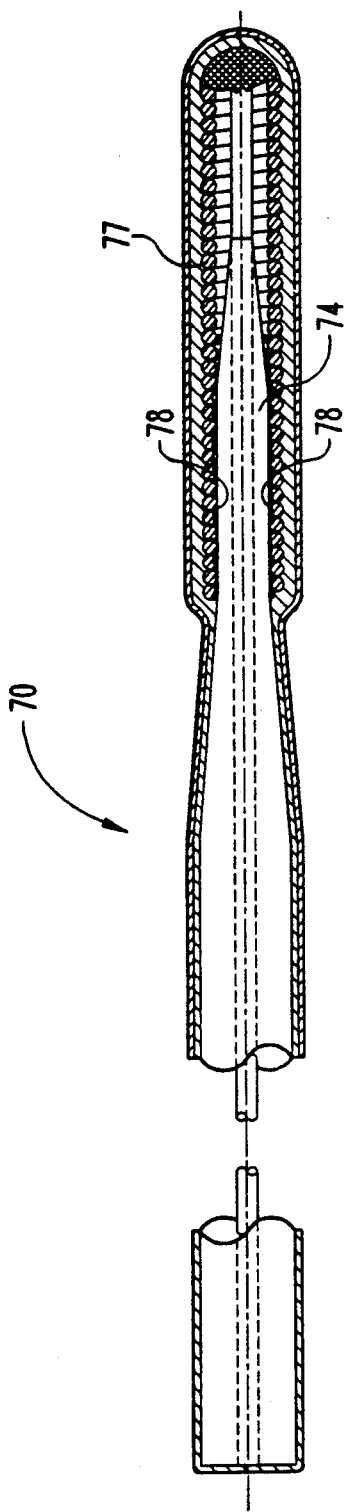
FIG. 7 is a fragmentary longitudinal sectional view of a wire guide according to still another embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to FIG. 1, there is shown a wire guide 10 according to the preferred embodiment of the present invention. Wire guide 10 includes a mandrel 11 which is a coaxial composite of shape memory material 12, such as a nickel titanium alloy, and an inner strand of readily weldable material, such as stainless steel. When referring to a "readily weldable material," the applicant means any material which cannot properly be classified as a shape memory material and which can easily be welded to other like materials. In this case, readily weldable material 13 could also be a radiopaque material such as platinum or gold. Wire guide 10 also includes coil spring 17, which is preferably formed of a radiopaque material such as platinum. A radiopaque element near the distal end of the wire guide better enables the physician using the wire guide to determine its exact location via x-rays.

Mandrel 11 includes a section 14 having a substantially uniform diameter over the majority of its length and a tapered section 15 that leads to a second uniform diameter section 16. Section 16 consists solely of the readily weldable material 13. Coil 17 is bonded to tapered section 15 at fastening location 18 by some conventional means such as gluing, soldering or possibly by a crimping process. Coil 17 coaxially surrounds the distal end of mandrel 11 but does not extend to any significant distance beyond the tip 20 of mandrel 11. Welded to tip 20 is a smoothly rounded cap 19, which is also preferred to be some readily weldable material, such as stainless steel. One of the advantages of the present invention is a wire guide that includes a kink resistant body and a reliable attachment between the distal tip of the mandrel and the end cap, which serves to reliably secure the coil spring in place and also shields the coils leading edge. Because tip 20 is solely formed of a readily weldable material, instead of an NiTi alloy, there is no need to include a safety wire connection between the end cap and the mandrel to ensure that the cap stays attached to the remainder of the wire guide during the insertion and retrieval process involving a live patient. Finally, the entire wire guide is covered by polymer coating 21, such as polyurethane, which bonds well to the underlying metallic surfaces but also provides good base for hydrophilic coating 22, which provides lubricity to ease insertion of the wire guide. Hydrophilic coating 22 preferably extends along most of the wire guide except for the 20 to 30% of the wire guide near the proximal end to ensure an adequate gripping surface at the proximal end which is free of the hydrophilic coating. Candidates for the hydrophilic coating include but are not limited to polyvinylpyrrolidone or polyethyleneoxide.

Wire guides according to the present invention range in length from 20 to 460 centimeters with diameters in the uniform diameter section 14 typically ranging from 0.012 to 0.065 inches. The diameter of the readily weldable material 13 is generally significantly smaller than the overall diameter of the wire guide, as illustrated for instance in FIG. 2. In all the embodiments shown, the mandrel is made up of at least half shape memory material. The combined length of tapered section 15 and uniform diameter section 16 ranges from 1 to 30 centimeters, depending upon the desired flexibility at the distal end, but more typically ranges in length from 10 to 15 centimeters in most applications. Platinum coil 17 typically ranges from 2 to 3 centimeters in length but can vary from 1 to 15 centimeters in length for nontypical applications.

Referring now to FIG. 2, there is shown a cross section of the wire guide 10 of FIG. 1 taken along line A—A in the direction of the arrows. Mandrel 11 comprises a coaxial composite of readily weldable material 13 surrounded by a shape memory material 12. Also shown is a cross section of polymer coating 21 and hydrophilic coating 22. FIGS. 3 and 4 show two possible variations of composite mandrels comprising a fusion of readily weldable material and a shape memory material. In the case of FIG. 3, mandrel 30 comprises a side-by-side composite of readily weldable material 32 and shape memory material 31. FIG. 4 shows a mandrel 35 that is an eccentric composite of readily weldable material 37 which is off center with but surrounded by the shape memory material 36.

FIG. 5 shows a wire guide 40 according to another embodiment of the present invention. Guide 40 includes a mandrel 41 which is a coaxial composite of readily weldable material 43 surrounded by shape memory material 42. Mandrel 41 includes a first section 44 which is of substantially uniform diameter and extends over a majority of the wire guide s length. Near its distal end, mandrel 41 includes first and second tapered sections 45 and 47 respectively, and second and third uniform diameter sections 46 and 48 respectively, which consist solely of the readily weldable material 43. The lengths and diameters of these various sections can be varied to achieve the desired stiffness and flexibility at the distal end of the wire guide. Attached to tapered section 45 at fastening location 50 is coil spring 49, which is preferably formed from a radiopaque material such as platinum. The distal end of coil spring 49 and mandrel 41 is shielded by smoothly rounded hemispherical tip 51 which is welded to the distal end 52 of mandrel 41. Finally, like the embodiment shown in FIG. 1, the entire length of the wire guide is coated with a polymer coating 53, and a hydrophilic coating 54 covers the portion of the wire guide which will enter the body of the patient during the insertion process. Both coatings can be applied by known methods, such as by spraying or dipping.

FIG. 6 shows a wire guide 60 according to another embodiment of the present invention. Guide 60, like the embodiments described earlier, includes a coaxial composite mandrel 61. In this case, mandrel 61 includes a step portion 62 which is immediately proximal to tapered portion 63. Step 62 abuts the proximal end of spring coil 64, which is attached to mandrel 61 at fastening location 65 by crimping, soldering, gluing or some other suitable means. Step 62 permits a smoother transition from the outer surface of coil 64 to the outer surface of mandrel 61. Wire guide 60 also includes a smoothly rounded cap 66 that is welded to the distal tip 67 of mandrel 61. The entire length of wire guide 60 is then coated with a first polymer layer 68, and the distal 70 to 80% of the wire guide is coated with hydrophilic coating 69.

FIG. 7 shows a wire guide 70 according to still another embodiment of the present invention. In many respects, the guide is identical to those described above, except guide 70 includes a uniform diameter section 74 which is substantially equal to the inner diameter of coil spring 77. Uniform diameter section 74 results in an improved bonding connection 78 between the mandrel and the coil spring. The bonding connection 78 is better and stronger because it extends for a substantial length unlike the connection 50 of FIG. 5, for example, which mates a taper to a constant diameter. Bonding of connection 78 is accomplished by gluing or soldering. The various tapered and uniform diameter sections of the embodiments shown and described can be formed by grinding methods that are well known in the art.

Figure 8:
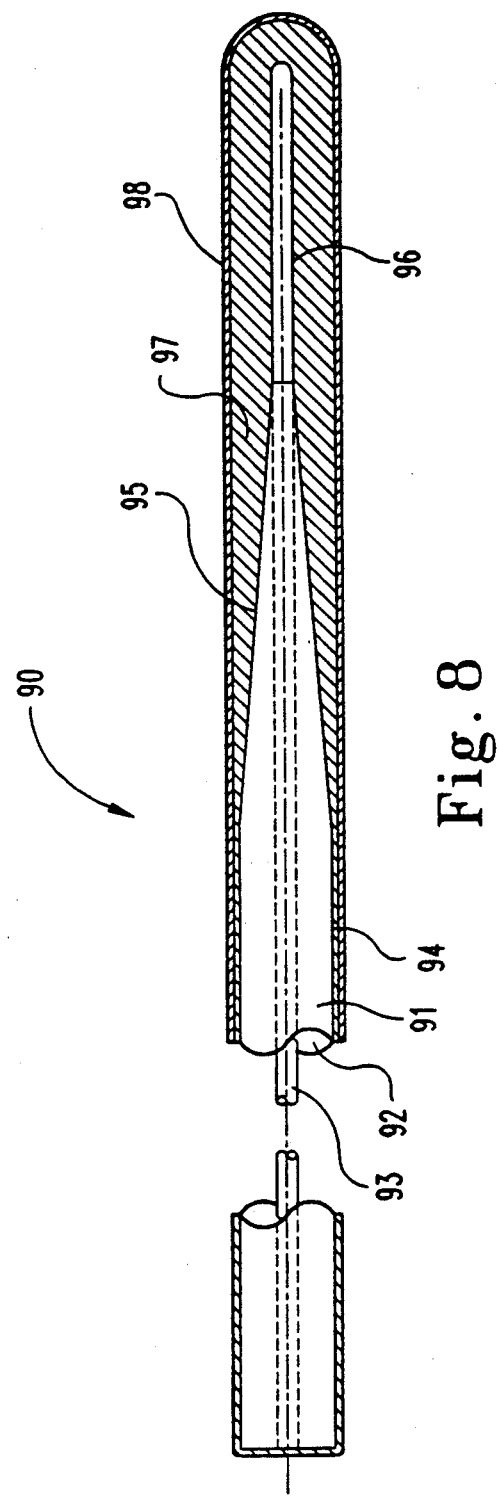
FIG. 8 is a fragmentary longitudinal sectional view of a wire guide according to another embodiment of the present invention.

FIG. 8 shows a wire guide 90 according to an embodiment of the present invention that does not include a coil spring at its distal end. Guide 90 includes a mandrel 91 which is a coaxial composite of readily weldable material 93 surrounded by shape memory material 92.

Mandrel 91 includes a substantially uniform diameter section 94 over the majority of its length but also includes tapered section 95 and uniform diameter section 96 at the mandrel's distal end. Like the embodiments described above, the entire length of the wire guide is coated with a polymer layer 97. However, in the present embodiment, the polymer coating 97 is thicker at the distal end to give the overall wire guide a substantially uniform diameter, removing the discontinuities along its length that might otherwise exist. The shapes (lengths and diameters) of tapered section 95 and uniform diameter section 96, as well as the thickness of polymer layer 97, can be varied to produce a desired flexibility in the distal end of the wire guide. Guide 90 also includes a hydrophilic coating 98 over the distal 70 to 80% of the wire guide for lubricity.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A composite mandrel for a wire guide comprising:
   a strand of readily weldable material radially surrounded by and fused with a shape memory material; and
   wherein at least half of the mandrel is made up of said shape memory material.

2. The composite mandrel of claim 1 wherein, said strand and said shape memory material are concentric.

3. The composite mandrel of claim 2 wherein, said shape memory material is a nickel titanium alloy.

4. The composite mandrel of claim 3 wherein, said readily weldable material is stainless steel.

5. The composite mandrel of claim 3 wherein, said readily weldable material is also radiopaque.

6. A composite mandrel for a wire guide comprising:
   a strand of readily weldable material radially surrounded by and fused with a shape memory material;
   wherein said strand and said shape memory material are concentric;
   wherein said shape memory material is a nickel titanium alloy;
   wherein said readily weldable material is also radiopaque; and
   wherein said readily weldable material includes significant amounts of gold or platinum.

7. A wire guide comprising:
   a solid mandrel that is a composite of a shape memory material and a readily weldable material, said mandrel having a distal end, a proximal end and defining an axis extending between said ends;
   a flexible coil coaxially surrounding a portion of said distal end of said mandrel about said axis; and
   a smoothly rounded tip welded to said distal end of said mandrel distally of said flexible coil.

8. The wire guide of claim 7 wherein, said shape memory material radially surrounds said readily weldable material.

9. The wire guide of claim 8 wherein, said shape memory material is coaxial with said readily weldable material.

10. The wire guide of claim 9 wherein, said shape memory material is a nickel titanium alloy.

11. The wire guide of claim 10 wherein, said readily weldable material is stainless steel.

12. The wire guide of claim 11 wherein, said flexible coil is formed of a radiopaque material.

13. The wire guide of claim 12 wherein, said radiopaque material is platinum.

14. The wire guide of claim 10 wherein, said readily weldable material is also a radiopaque material.

15. The wire guide of claim 9 wherein, said mandrel includes a first substantially uniform diameter section, a first tapered section adjoining said first uniform diameter section and a second substantially uniform diameter section adjoining said first tapered section, and said second uniform diameter section consists only of said readily weldable material, said flexible coil radially surrounds said second uniform diameter section and radially surrounds a portion of said first tapered section.

16. The wire guide of claim 9 wherein, said mandrel includes serially attached to one another a first substantially uniform diameter section, a first tapered section, a second substantially uniform diameter section, a second tapered section and a third substantially uniform diameter section distal of said second uniform diameter section, and said third uniform diameter section consists only of said readily weldable material, said flexible coil radially surrounds said second uniform diameter section and radially surrounds a portion of said first tapered section.

17. The wire guide of claim 9 wherein, said mandrel includes a first substantially uniform diameter section separated from a first tapered portion by a radial step portion and a second substantially uniform diameter section adjoining said first tapered section; and
said flexible coil abuts against said radial step portion.

18. The wire guide of claim 9 wherein, said mandrel includes serially attached to one another a first substantially uniform diameter section, a first tapered section, a second substantially uniform diameter section, a second tapered section and a third uniform diameter section, and said third uniform diameter section consists only of said readily weldable material, said flexible coil radially surrounds said third uniform diameter section; and
said flexible coil has an inner diameter approximately equal to said second uniform diameter section, and said second uniform diameter section is received within said flexible coil.

19. A wire guide comprising:
   a mandrel that is a composite of a shape memory material and a readily weldable material, said mandrel having a distal end, a proximal end and defining an axis extending between said ends;
   a flexible coil coaxially surrounding a portion of said distal end of said mandrel about said axis;
   a smoothly rounded tip welded to said distal end of said mandrel distally of said flexible coil;
   a first polymer coating over the entire length of the wire guide; and
   a second hydrophilic coating over a portion of said first polymer coating.

20. The wire guide of claim 19 wherein, the wire guide has a distal half and said hydrophilic coating covers at least said distal half.

21. A wire guide comprising:

a mandrel that is a composite of a shape memory material and a readily weldable material, said mandrel having a distal end, a proximal end and defining an axis extending between said ends;

a flexible coil coaxially surrounding a portion of said distal end of said mandrel about said axis;

a smoothly rounded tip welded to said distal end of said mandrel distally of said flexible coil;

wherein said shape memory material radially surrounds said readily weldable material;

wherein said shape memory material is coaxial with said readily weldable material;

wherein said shape memory material is a nickel titanium alloy;

wherein said readily weldable material is also a radiopaque material; and wherein said readily weldable material contains a significant amount of gold or platinum.

22. A wire guide comprising:

a mandrel that is a composite of a shape memory material and a readily weldable material, said mandrel having a distal end and a proximal end, said mandrel having a substantially constant diameter portion over a majority of its length but tapered down to a smaller diameter portion at said distal end;

a first polymer layer over the entire length of the wire guide, and a second hydrophilic coating over a portion of said first polymer layer.

23. The wire guide of claim 22 wherein, said first polymer layer is sufficiently thick at said distal end to build up said smaller diameter portion to substantial equality with said constant diameter portion.

24. The wire guide of claim 23 wherein, said shape memory material radially surrounds said readily weldable material.

25. The wire guide of claim 24 wherein, said shape memory material is coaxial with said readily weldable material.

26. The wire guide of claim 25 wherein, said shape memory material is a nickel titanium alloy.

27. The wire guide of claim 26 wherein, said readily weldable material is stainless steel.

28. The wire guide of claim 27 wherein, said flexible coil is formed of a radiopaque material.

29. The wire guide of claim 28 wherein, said radiopaque material is platinum.

* * * * *